United States Patent [19]
Zinnbauer et al.

[11] Patent Number: 5,565,122
[45] Date of Patent: Oct. 15, 1996

[54] SUTURE CUTTING AND CAUTERIZING METHOD USING RADIANT HEAT

[75] Inventors: Gerald Zinnbauer, Charlotte, N.C.; Eric Hulsman, 1006 Countryside La., Smyrna, Ga. 30080; Brad Wellington, 887 Westmont Dr., Asheboro, N.C. 27203

[73] Assignees: Eric Hulsman, Smyrna, Ga.; Brad Wellington, Asheboro, N.C.

[21] Appl. No.: 456,529

[22] Filed: Jun. 1, 1995

Related U.S. Application Data

[62] Division of Ser. No. 268,253, Jun. 29, 1994, Pat. No. 5,452,513.

[51] Int. Cl.6 ............................ A61B 17/04; B25F 3/00
[52] U.S. Cl. .................... 219/227; 606/45; 606/228; 606/28; 606/138; 30/140; 30/124; 83/15; 264/138
[58] Field of Search ................................ 219/227, 229, 219/221, 225, 243; 606/27, 28–31, 39, 45, 228, 231, 138; 30/140, 124; 83/170, 171, 15, 16; 156/510, 515, 579, 250–251; 425/DIG. 13; 264/152, 157, 160, 138

[56] References Cited

U.S. PATENT DOCUMENTS

| | | | |
|---|---|---|---|
| 3,354,478 | 11/1967 | Allen | 30/140 |
| 3,769,396 | 10/1973 | Espinosa | 264/157 |
| 3,772,127 | 11/1973 | James | 156/251 |
| 3,934,115 | 1/1976 | Peterson | 219/223 |
| 4,030,743 | 6/1977 | Warthen | 83/15 |
| 4,285,753 | 8/1981 | Warthen | 156/251 |
| 4,516,574 | 5/1985 | Hewes, Jr. | 30/140 |
| 4,540,873 | 9/1985 | Kester | 219/200 |
| 4,662,068 | 5/1987 | Polonsky | 30/124 |
| 4,823,025 | 5/1989 | Coates | 606/228 |
| 5,160,077 | 11/1992 | Sticklin | 225/38 |
| 5,374,278 | 12/1994 | Chesterfield et al. | 606/228 |
| 5,417,700 | 5/1995 | Egan | 606/228 |
| 5,452,513 | 9/1995 | Zinnbauer et al. | 30/140 |
| 5,472,654 | 12/1995 | Crawford | 219/227 |
| 5,845,851 | 7/1989 | Warthen | 30/140 |

FOREIGN PATENT DOCUMENTS 8601759  3/1986  WIPO ............................... 83/170

*Primary Examiner*—John A. Jeffery
*Attorney, Agent, or Firm*—Rhodes Coats & Bennett, L.L.P.

[57] ABSTRACT

A suture cutter which is adapted to clamp, sever and cauterize a thermoplastic suture includes a housing having an electrical power source located in the housing and a trigger attached to the housing having open and closed positions. A suture clamp is attached to the housing and includes a stationary jaw and a pivotal jaw. A radiant heating element is adjacent to the suture clamp. An actuator connects the trigger to the pivotal jaw and electrical circuitry joins the power source to the radiant heating element. Closing of the trigger first closes the pivotal jaw against the stationary jaw to hold a suture, and then completes the circuitry to sever and cauterize the suture with radiant heat.

3 Claims, 3 Drawing Sheets

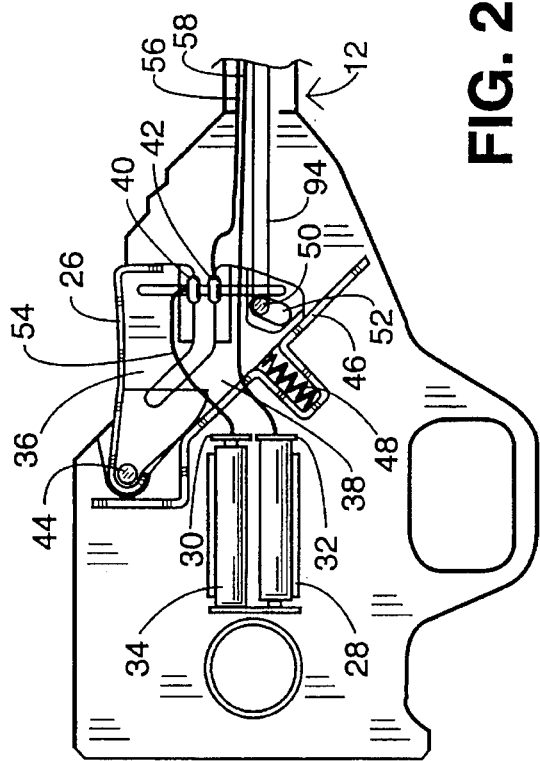
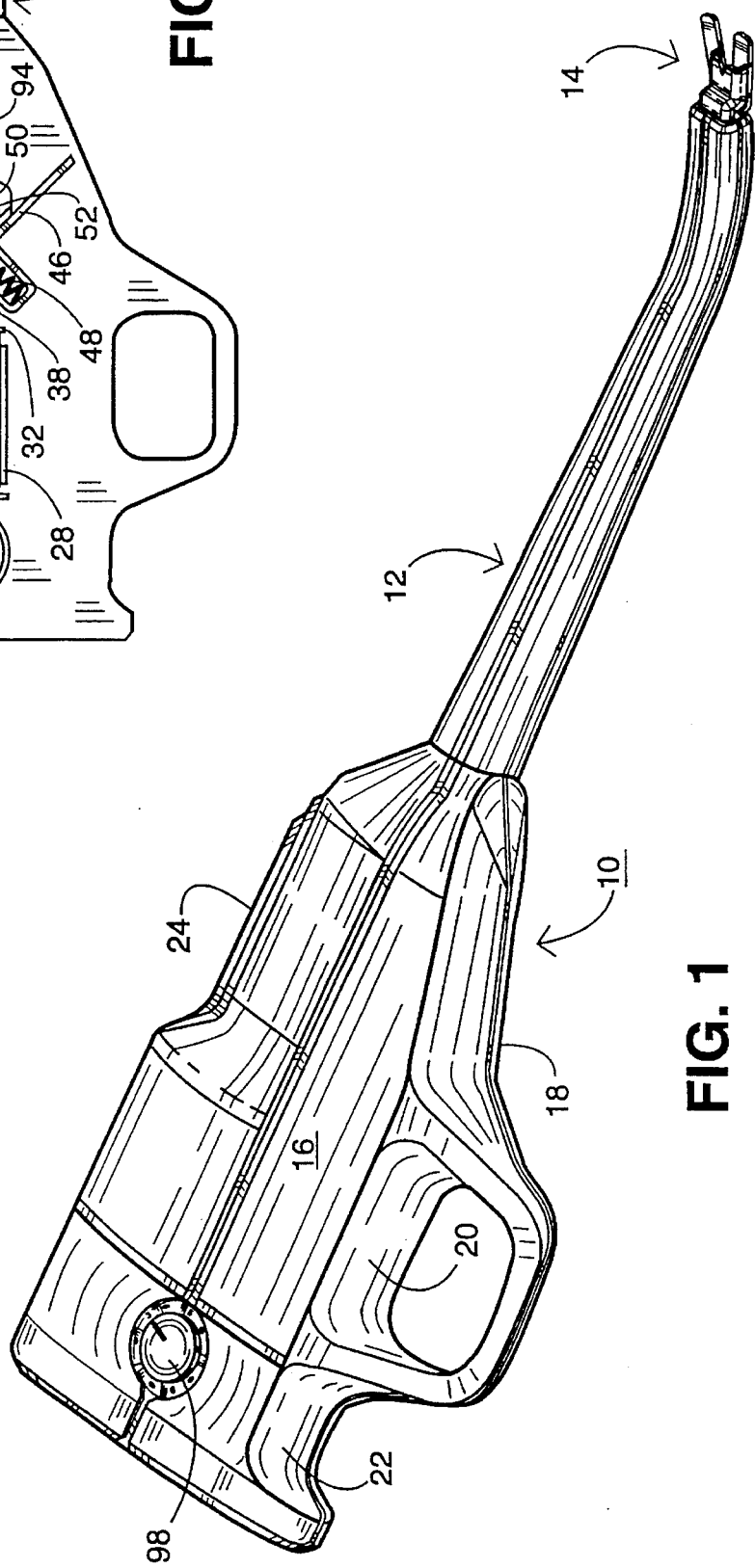
FIG. 2
FIG. 1

SUTURE CUTTING AND CAUTERIZING METHOD USING RADIANT HEAT

This application is a division of application Ser. No. 08/268,253, filed Jun. 29, 1994, and now U.S. Pat. No. 5,452,513, issued Sep. 26, 1995.

BACKGROUND OF THE INVENTION

(1) Field of the Invention

The present invention relates generally to suturing and, more particularly, to a method and apparatus for precisely cutting and fusing thermoplastic surgical sutures.

(2) Description of the Prior Art

Conventionally, individual sutures are first tied and then cut after they are applied. Surgical knots tied with smooth thermoplastic materials such as nylon require great care to ensure the knot does not loosen after closing. This is particularly difficult in delicate surgical procedures such as pediatric heart surgery because of the small size of the patient.

U.S. Pat. No. 4,662,068, issued to Polonsky, discloses a suture fusing and cutting apparatus having a forcep-type instrument with jaws including a cutting edge and a fusing surface. The jaws are heated electrically to sever and fuse the plastic suture when the jaws are closed on the suture. However, the heated fusing surface of the apparatus taught by Polonsky may come into contact with the tissues of the patient and cause burns.

Thus, there remains a need for a new and improved suture cutter which will precisely cut and fuse thermoplastic surgical sutures while, at the same time, prevent contact between the fusing element and the tissues of the patient.

SUMMARY OF THE INVENTION

The present invention is directed to a suture cutter which is adapted to clamp, sever and cauterize a thermoplastic suture. The suture cutter includes a housing having an electrical power source located in the housing and a trigger attached to the housing having open and closed positions. A suture clamp is attached to the housing and includes a stationary jaw and a pivotal jaw. A radiant heating element is adjacent to the suture clamp. An actuator connects the trigger to the pivotal jaw and electrical circuitry joins the power source to the radiant heating element. Closing of the trigger first closes the pivotal jaw against the stationary jaw to hold a suture, and then completes the circuitry to sever and cauterize the suture with radiant heat.

Accordingly, one aspect of the present invention is to provide a suture cutter adapted to clamp, sever and cauterize a thermoplastic suture. The suture cutter includes: (a) a hand grip section including a housing, a power source and a trigger having open and first and second closed positions; (b) a tip section including a housing, a suture clamp, and a radiant heating element; (c) a neck section having one end integral with the hand grip section housing and an opposite end integral with the tip section housing; (d) an actuator extending through the neck section and connecting the trigger to the clamp; and (e) electrical circuitry extending through the neck section and joining the power source to the radiant heating element, the trigger being interposed in the circuitry; whereby closing of the trigger first closes the clamp to hold a suture, and then completes the circuitry to sever and cauterize the suture with radiant heat.

Another aspect of the present invention is to provide a suture cutter adapted to clamp, sever and cauterize a thermoplastic suture. The suture cutter includes: (a) a housing; (b) an electrical power source located in the housing; (c) a trigger attached to the housing having open and closed positions; (d) a suture clamp attached to the housing; (e) a radiant heating element adjacent to the suture clamp; (f) an actuator connecting the trigger to the clamp; and (e) electrical circuitry joining the power source to the radiant heating element, the trigger being interposed in the circuitry; whereby closing of the trigger first closes the clamp to hold a suture, and then completes the circuitry to sever and cauterize the suture with radiant heat.

Still another aspect of the present invention is to provide a suture cutter adapted to clamp, sever and cauterize a thermoplastic suture. The suture cutter includes: (a) a housing; (b) an electrical power source located in the housing; (c) a trigger attached to the housing having open and closed positions; (d) a suture clamp attached to the housing, the suture clamp including a stationary jaw and a pivotal jaw; (e) a radiant heating element adjacent to the suture clamp; (f) an actuator connecting the trigger to the pivotal jaw; and (e) electrical circuitry joining the power source to the radiant heating element, the trigger being interposed in the circuitry; whereby closing of the trigger first closes the pivotal jaw against the stationary jaw to hold a suture, and then completes the circuitry to sever and cauterize the suture with radiant heat.

These and other aspects of the present invention will become apparent to those skilled in the art after a reading of the following description of the preferred embodiment when considered with the drawings.

BRIEF DESCRIPTION OF THE DRAWINGS

FIG. 1 is a schematic, perspective view of the suture cutter of the present invention;

FIG. 2 is a sectional plan view of the suture cutter hand grip section with part of the outer case removed to show the interior components;

DESCRIPTION OF THE PREFERRED EMBODIMENTS

Figure 4:
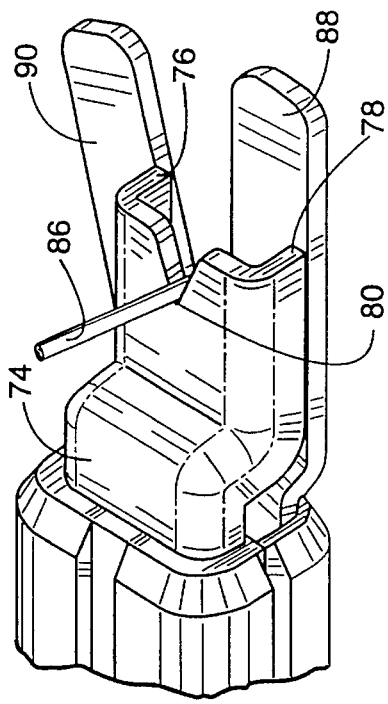
FIG. 4 is a detail view of the suture jaws in the open position with a suture in position to be severed and cauterized.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto.

As best seen in FIG. 1, the present invention is comprised of a molded plastic housing having a hand grip section 10, which also serves as a housing for a power source and a control mechanism, a tip section 14 distant from hand grip section 10, and an elongated neck section 12 having a front end integral with the hand grip section 10 and a rear end integral with tip section 14.

To aid in comfort of operation, tip section 14 is desirably at an angle, e.g., from 20° to 45° to neck 12. For example, in the illustrated preferred embodiment, tip 14 extends upwardly at an angle of about 30° above the horizontal from neck section 12.

Hand grip section 10 is designed to provide comfort and a steady grip for the user and includes a palm rest area 16, a rest 18 for the first and second fingers, an rest 20 for the third finger, a rest 22 for the fourth finger, and a thumb rest 24. A control trigger 26 used to activate the cutter is positioned in thumb rest 24 for easy access.

The interior of hand grip section 10, as shown in FIG. 2, contains a mounting bracket 28 having a pair of terminals 30 and 32, which is used to hold a source of power source, e.g. batteries 34.

Trigger 28 is formed from a flexible material, e.g., plastic, and is comprised of an outer arm 36 and an inner arm 38 spaced from arm 36. A first contact 40 is mounted on arm 36 and a second contact 42 is mounted on arm 38 in a position to engage contact 40. Trigger 26 is mounted to pivot about a pin 44. Stop 46 limits the inward movement of trigger 26. A spring 48 is positioned to return trigger 26 to an open position. A jaw control pin 50 rides within a slot 52 in arm Electrical circuitry having trigger 26 interposed therein, connect batteries 34 to a suture heater in tip 14. This circuitry comprises an electrical wire 54 extending from terminal 30 to contact 40, a second electrical wire 56 extending from contact 42 through neck 12 to tip 14, and a third electrical wire 58 extending from terminal 32 through neck 12 to tip 14. It will be apparent to one skilled in the art that the connections to the terminals can be reversed.

Figure 3:
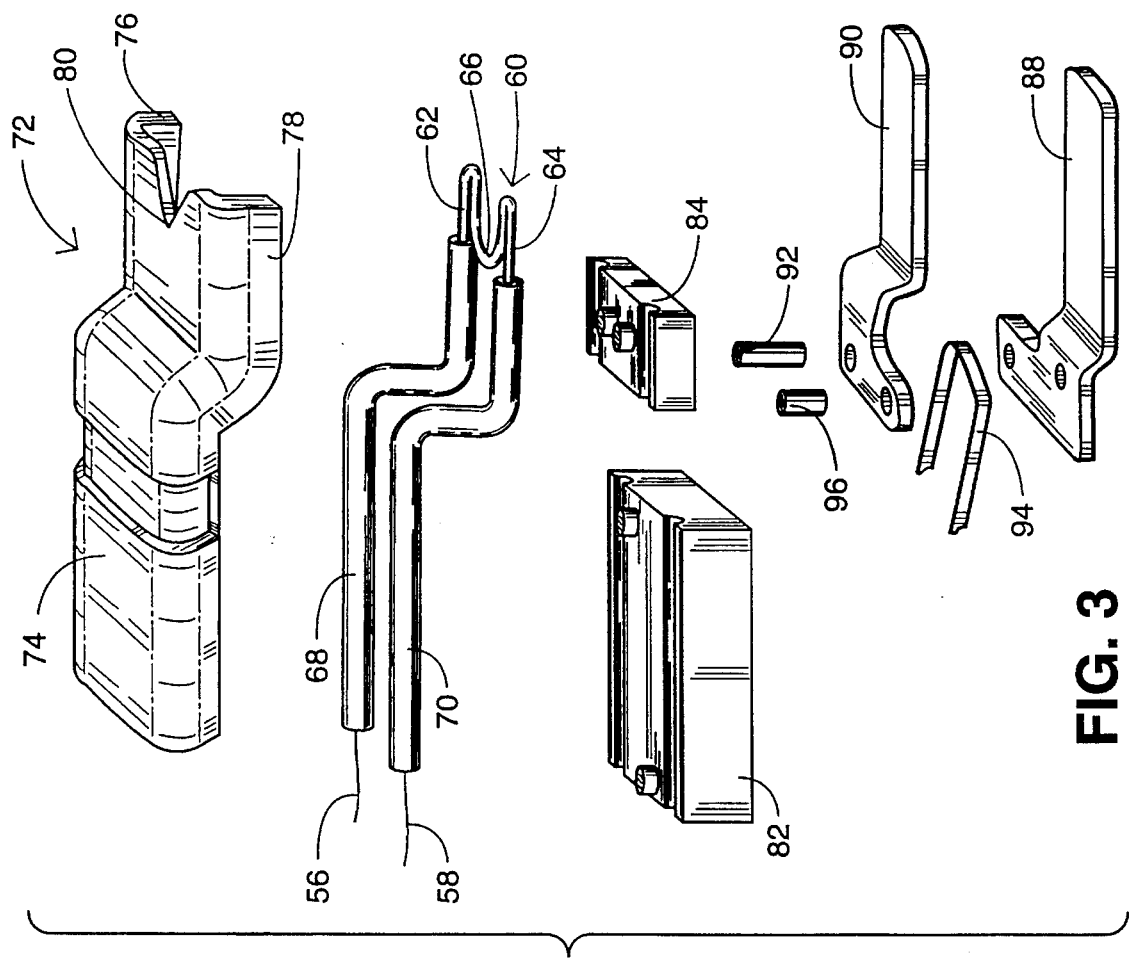
FIG. 3 is an exploded, schematic, perspective view of the suture cutter tip section.

As shown in FIG. 3, tip section 14 is comprised of a heating element, generally 60, which has a pair of rearwardly extending connector arms 62 and 64, and a central, rearwardly curved suture heating section 66 connecting arms 62 and 64. A pair of heater connectors 68 and 70 join arms 62 and 64 with wires 56 and 58, respectively to complete a circuit when trigger 26 is activated.

Heating element 60 is covered by housing 72, which is comprised of an upper wall 74 and a pair of side walls 76 and 78. Upper wall 74 includes a suture positioner in the form of a v-shaped slot 80 having an apex and perpendicular side walls at its outer end.

In the assembled suture cutter, heater connectors 68 and 70 are held within housing 72 by locking pieces 82 and 84, while section 66 of heating element 60 curves generally around the apex of receiving slot 80, without breaking the vertical plane of the walls of slot 80.

Figure 5:
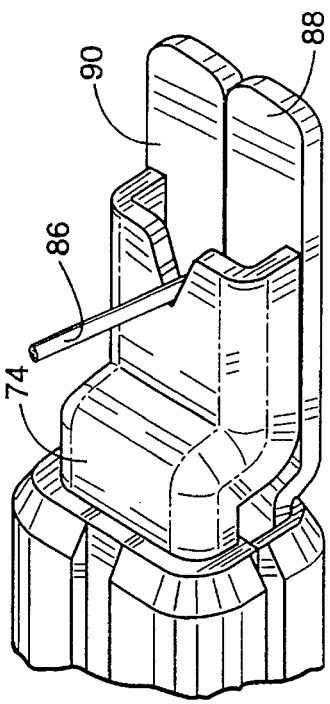
FIG. 5 is a detail view of the suture jaws in the closed position immediately after the suture has been severed and cauterized.

As best shown in FIGS. 4 and 5, a suture to be severed and cauterized by radiant heat from element 60 is positioned in slot 80, and held in position by a suture clamp comprised of a fixed jaw 88, and a pivotal jaw 90 which is pivotally mounted for rotation about a pin 92. An actuator 94 is also positioned around pins 92 and 96 which is attached to jaw 90, and extends rearwardly through neck section 12 into handgrip section 10 where it is positioned around pin 50.

In the preferred embodiment, the amount of electrical current flowing through the circuit can be varied as needed by a rheostat 98 within the circuit.

In operation, the user, while gripping hand grip 10, moves the suture to be cut into position in slot 80, and then depresses trigger 26. Initial movement of trigger 26 to a first position moves the edge of slot 52 against pin 50, and then forces pin 50 inwardly and upwardly, creating tension on actuator 94 which pulls against pin 92, closing pivotal jaw 90 against stationary jaw 88, to clamp the suture in position.

Further movement of trigger 26 to a second position causes arm 36 to flex inwardly bringing contact 40 against contact 42 to complete the electrical circuit. Electrical current then passes through heating element 60 to quickly heat the element to a high temperature. The heat radiating from element 60 quickly melts the suture to sever it while at the same time cauterizing the suture by forming a ball of molten material at the suture end, thus preventing the suture from being withdrawn.

Figure 6:
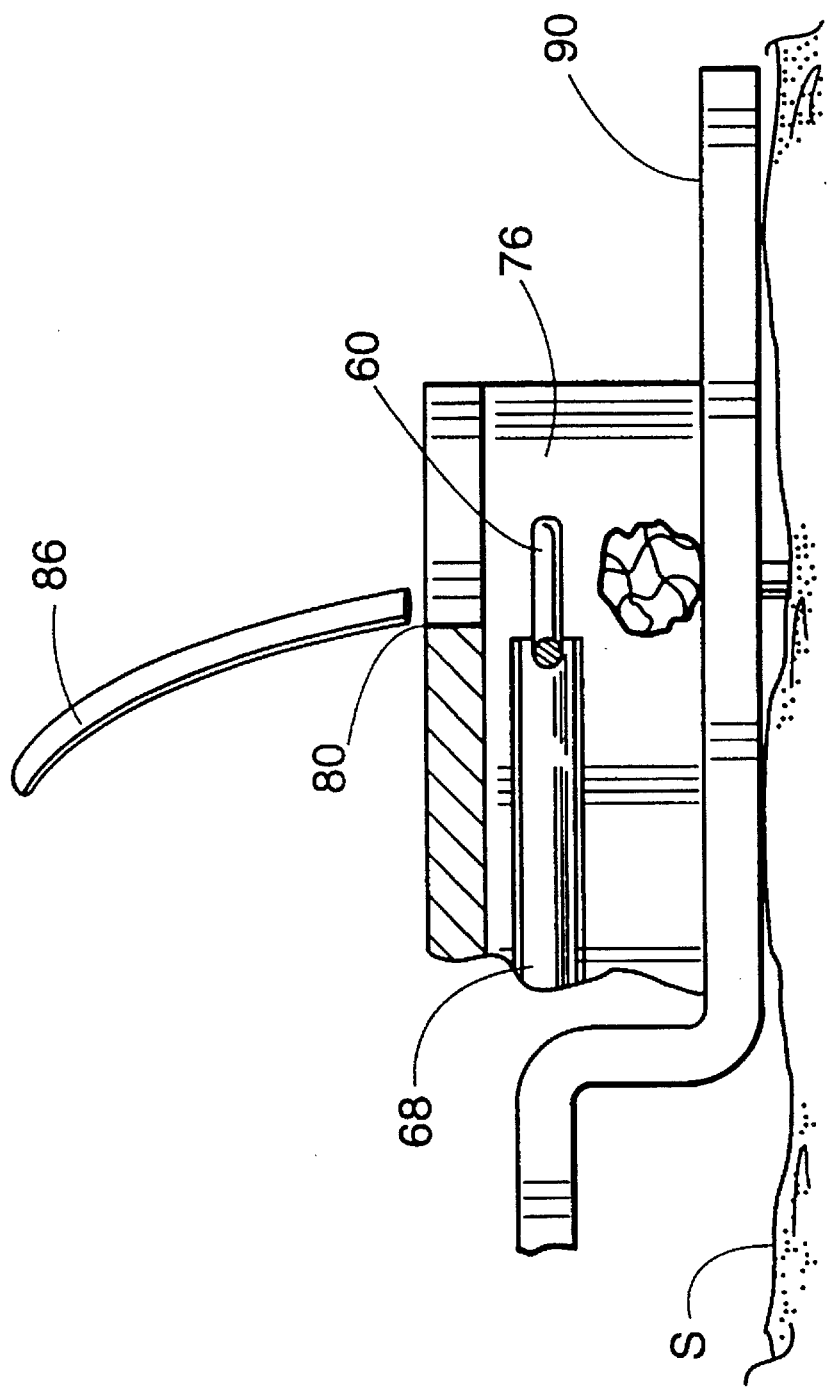
FIG. 6 is a sectional side view of the suture cutter tip immediately after cutting the suture, showing the ball of suture material and separation of the knot ball from the patient's skin by the jaws.

After the suture is severed and cauterized as shown in FIG. 6, the operator releases trigger 26 which, under the action of spring 48, returns to the first position to disengage contacts 40 and 42, stopping flow of current to heating element 60, and then returns trigger 26 to its original position, opening the suture clamp.

Certain modifications and improvements will occur to those skilled in the art upon a reading of the foregoing description. By way of example, different trigger configurations can be used, as well as different clamping arrangements where, e.g., both jaws are pivoted. Also, the shape of the case can be changed, or reversed to accommodate a left-handed operator. It should be understood that all such modifications and improvements have been deleted herein for the sake of conciseness and readability but are properly within the scope of the following claims.

We claim:

1. A method for severing and cauterizing a thermoplastic suture projecting from a patient's skin comprising:

(a) providing first and second clamping jaws;

(b) clamping said suture between said jaws at a clamping point above the patient's skin;

(c) radiantly heating said clamped suture at a heating point above said clamping point to sever and melt said suture, said heating point being opposite said clamping point from the patient's skin; and (d) releasing said suture.

2. The method according to claim 1, wherein said first jaw is stationary and said second jaw is pivoted toward said first jaw to clamp said suture.

3. The method according to claim 1, wherein said suture is melted to form a ball of suture material above said clamping point.

\* \* \* \* \*